(12) United States Patent
Schrock et al.

(10) Patent No.: US 7,164,749 B2
(45) Date of Patent: Jan. 16, 2007

(54) METHOD AND APPARATUS FOR MEAT SCANNING

(75) Inventors: Todd Schrock, Kingston, TN (US); Brook Nash, Walland, TN (US); Earl Smith, Seymour, TN (US)

(73) Assignee: Smiths Detection, Inc., Alcoa, TN (US)

( * ) Notice: Subject to any disclaimer, the term of this patent is extended or adjusted under 35 U.S.C. 154(b) by 373 days.

(21) Appl. No.: 10/876,761

(22) Filed: Jun. 28, 2004

(65) Prior Publication Data

US 2005/0287252 A1   Dec. 29, 2005

(51) Int. Cl.
   *G01N 23/06* (2006.01)
(52) U.S. Cl. .......................... 378/53; 378/57
(58) Field of Classification Search ................ 378/57, 378/53–54, 95; 366/151.1
   See application file for complete search history.

(56) References Cited

U.S. PATENT DOCUMENTS

| | | | |
|---|---|---|---|
| 4,171,164 A * | 10/1979 | Groves et al. ........... | 366/152.1 |
| 5,918,977 A | 7/1999 | Borggaard et al. | |
| 6,449,334 B1 | 9/2002 | Mazess et al. | |
| 6,866,832 B1 | 3/2005 | Garwood | |
| 2002/0110625 A1 | 8/2002 | Garwood | |
| 2003/0124221 A1 | 7/2003 | Garwood | |
| 2003/0152675 A1 | 8/2003 | Garwood | |
| 2003/0170358 A1 | 9/2003 | Garwood | |
| 2003/0182903 A1 | 10/2003 | Garwood | |
| 2003/0185947 A1 | 10/2003 | Garwood | |
| 2003/0215551 A1 | 11/2003 | Garwood | |
| 2004/0037932 A1 | 2/2004 | Garwood | |
| 2004/0146602 A1 | 7/2004 | Garwood et al. | |
| 2004/0185156 A1 | 9/2004 | Garwood | |

FOREIGN PATENT DOCUMENTS

| | | |
|---|---|---|
| GB | 2 332 613 A | 6/1999 |
| WO | WO 01/86272 A | 11/2001 |
| WO | WO 03/046533 A | 6/2003 |

OTHER PUBLICATIONS

"Simultaneous Fat, Weight, and Foreign Object analysis on-line'"Online! (Jun. 5, 2004) XP002345710; Retrieved from the Internet: URL:www.productinspection.co.uk/eagle_pipe_fa.pdf> retrieved on Feb. 13, 2005.
SafeFresh Technologies: The Gold Standard for Meat Processing & Packaging brochure, 4 pgs.

* cited by examiner

*Primary Examiner*—Edward J. Glick
*Assistant Examiner*—Hoon Song
(74) *Attorney, Agent, or Firm*—Foley & Lardner LLP

(57) ABSTRACT

A system and apparatus for scanning food products to determine at least one property of the food product. In one embodiment, two sources of the food product, such as a low fat and a high fat source, controllably feed into a grinder. The grinder feeds into an x-ray analysis apparatus which is adapted to determine the desired property of the food product by x-ray analysis. A controller then forms a feedback loop which controls the relative amount of food product being feed from each of the food product sources.

20 Claims, 2 Drawing Sheets

METHOD AND APPARATUS FOR MEAT SCANNING

BACKGROUND

The present invention relates generally to the field of x-ray inspection. More particularly the present invention relates to x-ray inspection of meat.

Inspection of various production products has become increasingly important in recent years. Traditionally, product inspection has been limited to physical inspection of the product by a worker on the production line. Obviously, this form of inspection is less than optimal. As such, two more useful devices were developed and became the standard inspection apparatus: a check weigher and a metal detector. Each of these devices has its own inherent limitations, and even the system in combination lacked the ability to provide much information. Therefore, a need exists for an inspection system that can provide more detailed and variable data. The types and breadth of inspection data needed vary from product to product.

One category of product for which inspection is especially important is food. Many properties of food need to be monitored and controlled such as but not limited to weight, temperature, amount of contaminants, nutrient levels, fat levels, and carbohydrate levels. In particular, the level of fat and carbohydrates included in diets is of concern in the current consumer market place. Awareness of fat intake has led consumers to value highly those food sources which are relatively low in fat or have virtually no fat content. This is especially true with respect to meat products or foods which contain animal-originating meat components. Meat products must be carefully inspected to ensure that the meat has the desired properties. Such properties include but are not limited to weight of the meat, meat tenderness, the effective atomic number of the meat, and the amount of contamination.

One characteristic which has become increasingly important to monitor is the meat yield. Meat yield is a measure of the percentage of a sample of meat that is fat and the percentage of the sample of meat that is chemical lean. Lean meat and meat fat have different chemical compositions. Lean meat has a high concentration of moisture and protein and includes nitrogen and oxygen atoms which are of a greater atomic number than the carbon and hydrogen atoms which predominate in meat fat.

Although techniques for chemically analyzing food products, such as for determining the amount of fat, are well known, such laboratory techniques are time consuming and costly. Moreover, these techniques typically require that the product be physically or chemically broken down, consequently, only selected samples of the product can be analyzed, rather than each product. This diminishes the accuracy of the analysis since the quantities of substances and contaminants can vary from one product to another.

Based on these and other chemical differences between lean meat and meat fat, devices for non-destructively determining the quantitative relationship between meat components by gamma radiation (x-rays) are known in the art. Such devices are based on the principle that x-rays are affected by the various components of the material in distinct, measurable ways. In general, a typical basic x-ray device is a linear array comprising a high voltage power supply to power a x-ray tube wherein a beam of x-rays is directed at the product. The x-ray beam passes through the product to ultimately impinge upon a sensor or sensors, such as a row of detector diodes. Such x-rays devices typically then display an image of the material based on the x-rays. This image can provide valuable information which a normal optical image cannot. The formation of images due to light or X-ray differs. The major difference is that optical images are created by light reflection on the object surface and X-ray images are formed due to X-rays absorption by passing through a material. Thus, an optical image gives information about the object's surface and an X-ray image supplies information about the inner structure of the object.

An X-ray image is a silhouette, where the degree of transparency is dependent on the density, thickness and the atomic number of the material. Using the current technology this information can be separated and coded into a false color. The atomic number information is coded into the hue value of a color image in HIS (Hue, Intensity, Saturation) format. The mixed information about the thickness and the density is coded into intensity of a color. A certain percentage of X-ray energy is absorbed by the material due to a process known as electron ionization. The amount of energy absorbed depends on the density and atomic number of the material. As a result, the detected X-ray attenuation provides a picture of the absorbed energy on the irradiated objects. Due to the absorbed energy being relative to the atomic number, it can be used in the material discrimination process.

In general, the lower the atomic number, the more transparent the material is to the X-rays. Materials composed of elements with a high atomic numbers absorb radiation more effectively causing darker shadows in an X-ray image. Substances with low atomic numbers absorb less X-ray radiation, hence their shadowgraph appears a lighter color. The absorption of the X-ray radiation by a material is proportional to the degree of X-ray attenuation and is dependent on the energy of the X-ray radiation and the following material parameters: thickness, density, and atomic number The relationship between these values can be described by:

$$I_x = I_0 \exp\left[-\left(\frac{\mu}{\rho}\right)x\right]$$

Where,
$I_x$ Intensity of the X-ray radiation after passing through a material;
$I_0$ Intensity of the narrow beam monoenergetic X-ray radiation before passing through a material;
$\mu$ linear attenuation coefficient;
$\rho$ material density;
x mass thickness (obtained by multiplying the thickness t by the density $\rho$, i.e., x=t $\rho$).

An important component in the equation is the mass attenuation coefficient ($\mu/\rho$), which can be rewritten:

$$\frac{\mu}{\rho} = x^{-1} \ln\left(\frac{I_0}{I_x}\right)$$

The mass attenuation coefficient represents the penetration and the energy deposition by the photons in materials. This can be obtained by the measurement of $I_0$ and combination with the confirmed values of $I_x$ and x. Research has been directed to obtaining the mass attenuation coefficient for radiological interest, as this value is characteristic for each element, mixture and compound. The dependence of the X-ray attenuation on the atomic number relies on three phenomena: photoelectric effect, Compton effect and pair production. All three mechanisms demonstrate the quantum nature of X-ray radiation.

The color in an X-ray image indicates the type of material. To produce color X-ray images, the current system employs the two energy levels. The radiation of X-ray interacts with the object under inspection causing X-ray attenuation. The attenuation of low and high X-ray energy is determined on the representative X-ray detectors and processed to produce a color image. The two different X-ray energy levels are passed through the objects, which show characteristic drops in intensity corresponding to the absorption at particular energy levels. The intensity of the generated shadow of an object at two different energy levels is unequal; it is dependent on the density as well as the material type. The combination of the measurements at the two different energy levels together with the knowledge of X-ray interaction allows for the determination of the material.

One form of inspection that has been investigated is the use of dual energy x-ray absorption scanners. Dual energy refers to radiation at two or more bands of energy, emitted simultaneously or in succession, or as part of a broadband of polyenergetic radiation over the diagnostic imaging range. As is known in the art, the measurement of x-ray energy attenuated by an object in two distinct energy bands can be used to determine information about the photoelectric absorption and Compton scattering of the particular materials of the object.

Photoelectric absorption and Compton scattering are determined by the electron density and atomic number of the materials and are functions of the x-ray energy. The photoelectric effect is predominant at low X-ray energies and with high atomic numbers. When a quantum of radiation strikes an atom, it may impinge on an electron within an inner shell and eject it from the atom. If the photon carries more energy than is necessary to eject the electron, it will transfer this residual energy to the ejected electron in the form of kinetic energy. The probability of the photoelectric effect per atom can be described by the following relationship:

$$\sigma \propto \frac{Z^n}{E^{\frac{7}{2}}}$$

Where,
7=cross-section of the photon effect;
Z=atomic number of the irradiated substance;
n=varying exponent between 4 and 5 across E;
E=quantum of the X-ray energy (photon energy).

The Compton effect occurs primarily in the absorption of high X-ray energy and low atomic numbers. The effect takes place when high X-ray energy photons collide with an electron. Both particles may be deflected at an angle to the direction of the path of the incident X-ray. The incident photon having delivered some of its energy to the electron emerges with a longer wavelength. These deflections, accompanied by a charge of wavelength are known as Compton scattering. The probability of the Compton effect per atom is illustrated in Figure above and described by:

$$\sigma \propto \frac{Z}{E}$$

Accordingly, with two measurements of the object and two different energies, a proportion of two predefined materials of a composition can be identified.

It is important to note that a by-product of this calculation is that the total quantity of material measured is factored out and hence this measurement process is particularly suited for industrial applications where the measured produce varies in thickness, density or is highly inhomogeneous. It is important, too, to note that the existence of only two attenuation mechanisms of Compton scattering and photoelectric absorption means that additional measurements at third or fourth x-ray energies provide no new information in this method. Techniques using more than two energy measurements, insofar as they are different from the present modeling approach, may not produce this same benefit of eliminating sample mass effects. Dual energy x-ray absorption scanners produce output intensities at two different x-ray energies in different ways. An x-ray tube working at one voltage, for example 150 keV, will produce x-rays with energies from 150 keV down to 0 keV. To select two groups of x-ray energies from this distribution, two detectors may be used where each detector is capable of measuring one of the two groups of x-ray energies required. In a dual-energy X-ray system, the high and low energy level are employed to identify materials. Metals and other heavier elements strongly absorb the low X-ray energy radiation and lighter materials including organic materials tend to strongly absorb high X-ray energy radiation. Using this method the material can be distinguished into different categories, according the atomic number.

Thus, there is a need in the art for a system providing a more efficient and manageable method for producing food products with desired properties.

SUMMARY OF THE INVENTION

In general, the present invention relates to a system for inspecting food products that provides a more efficient and manageable method for producing food products with desired properties. One embodiment provides a method for inspecting and controlling properties of a food material. A first stream of the food material and a second stream of the food material are provided and mixed. The mixed food material is scanned with x-rays at two energy levels using a x-ray analysis unit. producing an array of values representative of the intensities of the x-rays at two energy levels;
    processing the array of values; and
    determining at least one property of the food material; and
    controlling at least one of the first stream and the second stream in response to determination of the property.

BRIEF DESCRIPTION OF THE DRAWINGS

FIG. 2b is a side view of the x-ray analysis unit of 2a.

FIG. 2c is a front view of the x-ray analysis unit of 2a.

DETAILED DESCRIPTION

Figure 1:
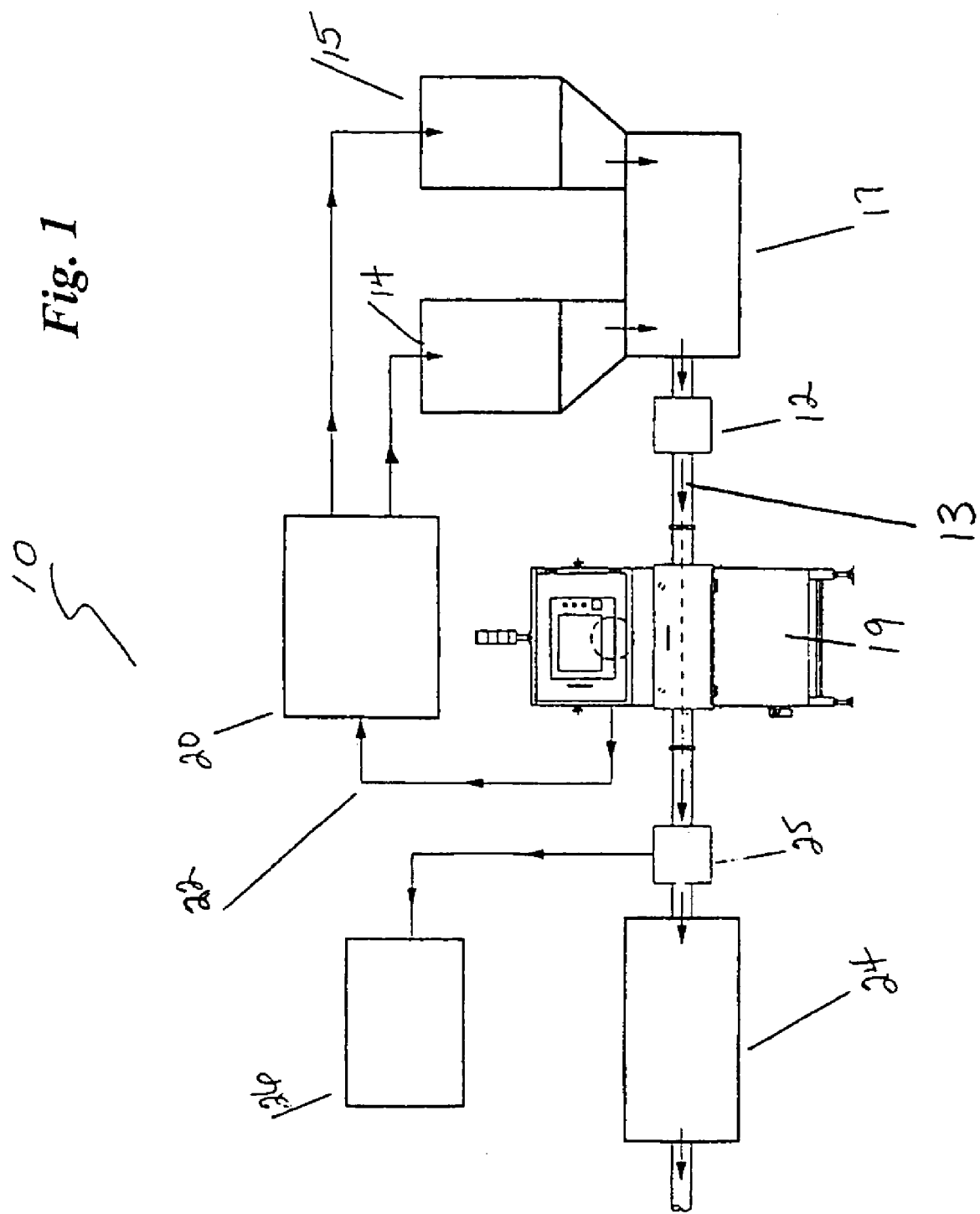
FIG. 1 is a flow chart depicting a system in accordance with the principles of the present invention.

A system in accordance with the principles of the present invention is capable of inspecting a food material, such as in one embodiment, meat. In reference to FIG. 1, a system 10 of the present invention as includes at least one mechanism for feeding the food material through the system 12 thus forming a food material stream 13, a first source of food material 14, a second source of food material 15, a x-ray analysis unit 19, a processor unit (not shown) a grinder unit 17, and a controller 20. In a preferred embodiment, the system 10 further includes a blender unit 24 and a rejected material area 26 whereby the food material stream 13 may be diverted from the blender unit to the rejected material area 26 by the use of a valve 28. The food material stream 13 is regulated to form a blended product having desired properties such as a desired fat percentage.

For illustrative purpose the following description often describes the present invention wherein the material being inspected is meat including beef, chicken, pork, lamb, deer, turkey, game bird, fish, and crustacean. Nevertheless, the invention should not be considered limited to meat and it should be understood that other food products could be utilized without departing from the scope of the invention.

More particularly, the feed mechanism 12 should supply the material as a material stream, preferably with generally consistent compaction or spacing and at a generally constant flow rate. The scope of the present invention includes a multitude of different mechanisms for feeding the food material through the system. For example, a positive displacement type pump (e.g., a gear pump) may be employed for less viscous-like food material. However, a gear pump is generally not preferred for more-viscous meats where a gear pump would introduce a relatively large error factor when pumping food materials which are resistant to being formed into a well-compacted stream moving at a relatively uniform velocity. In a preferred embodiment, the feed mechanism 12 includes a vacuum pump that pulls a vacuum to reduce air voids between the food material as it is being pumped. The reduction in the air voids reduces the errors in the x-ray analysis that can be caused by air pockets. In addition, heat may be used separately or in combination with the vacuum pump to further decrease air pockets and promote an adequate flow rate of the material stream. Conventional jacketed piping can be used for this purpose.

The pumping step includes moving the food material through the system and the various stages within the system. The pumping step can be sequential or continuous throughout a cycle of the present invention.

Alternatively, under some circumstances, the feed mechanism 12 need not include a pump. In one embodiment, a grinder unit 17 of the type commonly used in the trade may with suitable adaptations be used to provide the pumping action required by the system. The grinder unit 17 may be any suitable device capable of being adapted to receive the material from the feed mechanism 12. Preferably, the grinder unit 17 is adapted to receive a first food material from the first source and a second food material from the second source, whereby the first and second food materials differ in respect to at least one property. In one embodiment, the first food material source and the second food material source are distinct and separate inputs that contain relative lean meat and relative fat meat respectively. The grinding step comprises the receiving and mixing of the food material from the first food material source and/or the second material source either separately or simultaneously.

In one embodiment the x-ray analysis unit 19 incorporates radiation to determine the fat percentage of a moving meat stream as it passes through a pipe of known size. In one embodiment, the x-ray analysis unit 19 is adapted to perform the analysis and monitoring steps. The x-ray analysis unit 19 itself has a x-ray device comprising a source of x-rays, such as an x-ray tube, a first and second window, an analysis chamber, and at least one x-ray sensor. The x-ray device may comprise many existing x-ray systems that are known in the art for use in determining the composition of food materials, such as but not limited to dual energy x-ray systems. The x-ray tube can be collimated to produce an area, cone, pencil or fan beam. In one embodiment, a single dual energy x-ray detector module is used. A single dual energy x-ray detector module avoids the differential measurement errors due to pixel alignment problems. In addition, the use of a single detector module ensures that the measured areas are co-located in the product. The detectors and detection equipment enable the energies of the x-rays to be detected after transmission through the food material in the analysis chamber.

The food material, such as meat, enters the analysis chamber through a passage. The analysis chamber is preferably a pipe having first and second windows which permit the passage of radiation therethrough. In one embodiment, access to the pipe is gained through a traditional access means such as a sliding door, a rear access panel, and end plates. In one embodiment, the X-rays pass through the first window or aperture. Preferably the first window has a failsafe shutter which is interlocked with the feed pump and which automatically closes when the feed mechanism 12 stops in order to prevent continuous X-ray exposure while the stream 13 has stopped.

The x-ray device provides x-ray information to the processor unit. In one embodiment, the x-ray information is passed to the processor unit in terms of the intensity of the high and low energy x-ray beams after passing through the food material. The x-ray device provides a set of high and low energy measurements to the processor unit at multiple pixel locations over a detection area within the x-ray beam. In this embodiment, the multiple locations may be derived through the use of a linear or array-type detector or a scanning detector having one or a few detector elements.

In one embodiment, beams of X-ray radiation are passed through the food material stream, the beams being attenuated thereby, and the degree of attenuation being used to calculate fat percentages in accordance with known procedures, usually using attenuations of calibration standards corresponding to fat percentage values. The fat percentage at the beginning of any cycle is thereafter continuously integrated with subsequent fat percentage readings to obtain a continuously updated value for the fat percentage of the total quantity of meat analyzed since the beginning of the cycle. Preferably, an indicator light warns that the X-ray device is turned on.

In a preferred embodiment, the x-ray analysis unit 19 and processor units are capable of detecting foreign bodies or contaminants. This includes those having low density, such as plastic chips, as well as high density foreign bodies, such as metal burrs and stones.

In a preferred embodiment, a velocity sensor device monitors the food material stream 13 after it has passed through the X-ray analysis unit 19 and generates data useful in increasing the accuracy of the total system by being able to record how much meat has been pumped through the X-ray unit. The x-ray analysis unit 19 is in communication with the processor unit, which may be integrated with the x-ray analysis unit 19 or located separate.

In one embodiment, the intensity of the high and low energy x-ray beams after having passed through the food material is utilized as known in the art to determine the atomic number of the food material. For example, in one embodiment the effective atomic number of the food material is calculated as a sum of terms of the form $C_Z W_Z Z$ divided by the sum of the terms of form $C_Z W_Z$, where Z is the atomic number of each contributing element in the material matrix, $C_Z$ is the corresponding number of atoms per unit mass and $W_Z$ is a corresponding weight representing the relative measurement bias for this element. The measurement bias is determined from the physical principles underlying the measurement process. Many gauge systems employing x-rays have an enhanced sensitivity to higher atomic number elements, because the photo-absorption process is proportional to $Z_n/A$, where A is the nucleon number and "n" is theoretically as high as 5.

The processor unit receives data from or controls the feed mechanism 12, the X-ray unit, and the sensor device. The processor unit is in communication with a controller, which regulates a feedback loop wherein the information obtained in the x-ray analysis unit 19 is used to control the relative amounts of food material being feed from the first food material source and the second food material source. In one embodiment, a operation of the processor unit is to receive the percentage fat data and the weight data and from these to regulate the operation of the feed mechanism 12 for ultimately arriving at the desired fat percentage blend and, if also desired, the total formulation batch weight.

In one embodiment, the monitoring step uses a sensor to determine the amount of food material that has flowed during the analyzing step in arriving at the integrated fat percentage value. Such monitoring step can include weighing the food material previously analyzed. It can include, alternatively, measuring the velocity of the food material stream 13 to calculate the amount of meat thereby. Data accumulated in the monitoring step is incorporated with the fat percentage data, each with respect to both food material streams, into ratio relationships to calculate and project blended fat percentages and, if desired, blend weights. Monitoring step data can also be used to correct the analyzing step data for errors arising during that step from assumptions inherent in the analyzing step per se to the effect that the flow is at a constant rate of weight per unit time and that air voids have been removed from the stream.

After having completed analysis and monitoring in the x-ray analysis unit, the material then flows out of the x-ray analysis unit. In one embodiment, the material stream 13 is directed either to the blender unit 24 or to a rejected product area depending on the results of the analysis and monitoring steps. According to an embodiment of the present invention, the material stream 13 may be directed through an exit passage of the x-ray analysis unit to a valve which is in communication with the processor unit. The processor unit controls the opening of the valve, which in turn controls whether the material enters the blender unit 24 or the rejected product area.

The blender unit 24 blends the food material. The blending unit may be selected depending on the nature and quantity of the material as well as the desired properties of the end product. In the blending step, the streams are combined by conventional mixing techniques into the desired formulation. The processor unit uses data generated in the analyzing and monitoring steps to automatically and quickly set up and determine the ratios between fat percentages and amounts of meat and then uses these data to regulate the rate of the pumping step for one or both of the streams and to make corrections in the analyzing step data.

A method according to the present invention proceeds with continuous analysis and monitoring of substantially entire streams of meat combined into a meat blend having a desired fat percentage. It includes supplying meat in the form of a stream, continuously analyzing the stream 13 for fat content as it flows past a particular location, continuously monitoring the stream 13 for measuring the amount of meat analyzed, supplying another meat stream, analyzing and monitoring it in substantially the same manner, and automatically blending the two streams in proportions for arriving at a meat having a desired fat percentage.

In one embodiment, the X-ray inspection system of the present invention, using dual-energy techniques, determines the actual chemical lean value of the product pumped via pipe through the X-ray inspection system. A comparison with the customer inputted target chemical lean value dictates a control response from the dual-energy X-ray inspection system to the appropriate relative lean or relative fat meat source. The X-ray inspection system relies on a dual-energy response to acquire the signals for the algorithm that produces the chemical lean value.

Figure 2C:
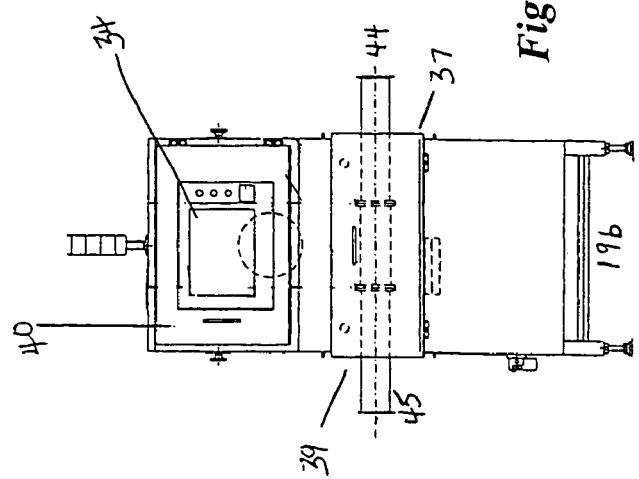
Figure 2A:
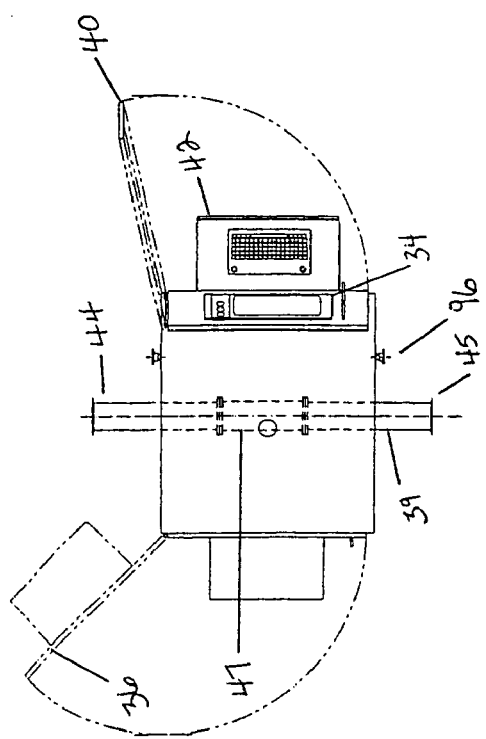
FIG. 2a is a top view of an x-ray analysis unit in accordance with the principles of the present invention.
Figure 2B:
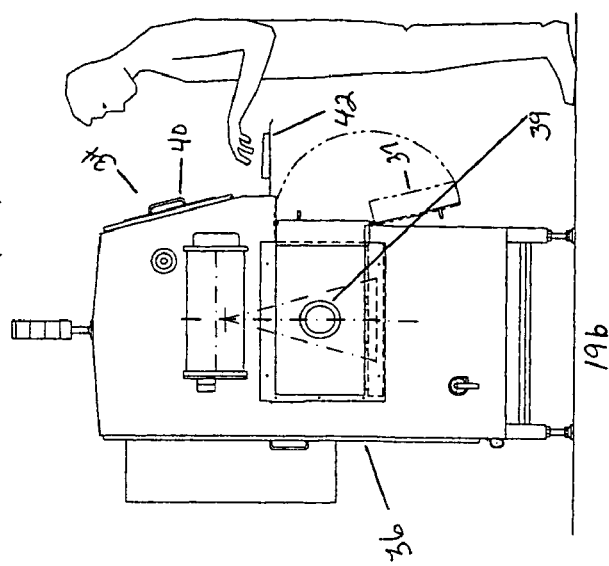

The x-ray analysis unit may comprise a user interface as depicted in FIGS. 2a–c. In one embodiment, the x-ray analysis unit 19b provides a video display unit 34 such as a LCD screen or a CRT television. The video display unit 34 may be protected by a transparent door 40. In addition, the x-ray analysis unit 19b may include a user input device 42 such as but not limited to a standard computer keyboard and mouse. In addition, in a preferred embodiment, the x-ray analysis unit provides axis doors 36, 37 to allow a user to access the passage 39 including the analysis chamber 47, the entrance passage 44 and the exit passage 45, which may all be parts of a continuous member such as a standard pipe, in the x-ray analysis unit.

When the actual chemical lean value of the product is within the acceptable chemical lean range, as inputted by the customer, the product is conveyed via pipe to a final blending unit. When the actual chemical lean value of the product is outside the acceptable chemical lean range, as inputted by the customer, the dual-energy X-ray inspection system provides a feedback signal to add lean or fat meat to control the output of the blender to the prescribed chemical lean value.

Also included in this application is the inspection of the product for physical contaminations such as metal, glass, stone, bone, and plastics. The inline valve is triggered to open, remove the suspect product, and close after disposal. In one embodiment, a system in accordance with the principles of the present invention is capable of detecting metal contaminants down to 2 mm spheres. In addition, the present invention may utilize a counter, to keep track of the number and type of each rejection.

In one embodiment, the present invention includes a barcode reader. The barcode reader may be adapted to allow a system in accordance with the principles of the present invention to differentiate boxes that are not intended for fat analysis, such as bone-in products.

What is claimed is:

1. A method for inspecting and controlling properties of a food material comprising:
   providing a first stream of the food material and a second stream of the food material;
   mixing the first stream and the second stream;
   scanning the mixed food material with x-rays at two energy levels using a x-ray analysis unit;

producing an array of values representative of the intensities of the x-rays at two energy levels;
processing the array of values; and
determining at least one property of the food material; and
controlling at least one of the first stream and the second stream in response to determination of the property.

2. The method of claim 1, wherein the step of determining includes determining the chemical lean value of the food material.

3. The method of claim 1, wherein the food material comprises meat.

4. The method of claim 3, wherein the meat is chosen from the group consisting of beef, chicken, pork, lamb, deer, turkey, game bird, fish, crustacean and mixtures thereof.

5. The method of claim 1, wherein the step of providing includes pumping the food material.

6. The method of claim 1, wherein the determining step includes determining the level of foreign contaminants within the food material.

7. The method of claim 6, further comprising the step of rejecting mixed food material having at least a predetermined level of contaminants.

8. The method of claim 1, further comprising the step of blending the food material after the step of scanning the mixed food material.

9. The method of claim 1, wherein the x-ray analysis unit comprises a single dual energy x-ray detector module.

10. The method of claim 1 further comprising the step of measuring physical properties of the food material stream taken from the group consisting of velocity, weight, temperature, and combinations thereof.

11. An apparatus for inspecting a food material comprising:
a grinder adapted to receive food material from first and second sources;
a blender for blending the food material;
an x-ray analysis unit having a dual energy x-ray and a substantially tubular passage which is in communication with the grinder and the blender, and
a controller for adjusting the ratio of the first and second sources of food material received by the grinder.

12. The apparatus of claim 11, wherein the controller is configured to analyze information from the x-ray analysis unit to derive a property of the food material.

13. The apparatus of claim 11, wherein the food material comprises meat.

14. The apparatus of claim 11, further comprising a valve between the x-ray analysis unit and the blender for diverting food material away from the blender to a rejected product area.

15. The apparatus of claim 11, further comprising a device for moving the food material within the apparatus.

16. The apparatus of claim 15, wherein the moving device includes a vacuum pump.

17. The apparatus of claim 11, wherein the x-ray analysis unit further comprises a video display unit.

18. The apparatus of claim 11, wherein the x-ray analysis unit comprises a single dual energy x-ray detector module.

19. A system for controlling the lean value of meat comprising:
a grinder adapted to receive a supply of lean meat and supply of fat meat;
a blender for blending the meat;
an x-ray analysis unit in communication with the grinder and the blender via a substantially tubular passage;
a controller for controlling the relative ratio of fat meat to lean meat sent to the grinder.

20. The system of claim 19, wherein the controller is configured to determine the chemical lean value of the meat in the x-ray analysis unit and to change the relative amount of fat meat to lean meat sent to the grinder based upon a predetermined target chemical lean value.

* * * * *

UNITED STATES PATENT AND TRADEMARK OFFICE
Certificate

Patent No. 7,164,749 B2                                                                  Patented: January 16, 2007

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Todd Schrock, Kingston, TN (US); Brook Nash, Walland, TN (US); Earl Smith, Seymour, TN (US); Robert Drummond Archibald, Christchurch (NZ); Colin Murray Bartle, Wellington (NZ); and John Gregory West, Lower Hutt (NZ).

Signed and Sealed this Eighth Day of September 2009.

<div style="text-align: right;">

EDWARD J. GLICK
*Supervisory Patent Examiner*
Art Unit 2882

</div>